United States Patent
Deshpande et al.

(10) Patent No.: US 9,724,311 B2
(45) Date of Patent: Aug. 8, 2017

(54) CURCUMIN COMPOSITIONS AND USES THEREOF

(71) Applicant: OmniActive Health Technologies Limited, Lower Parel, Mumbai (IN)

(72) Inventors: Jayant Deshpande, Charlottetown (CA); Vijaya Juturu, Morristown, NJ (US)

(73) Assignee: OmniActive Health Technologies Limited, Mumbai (IN)

( * ) Notice: Subject to any disclaimer, the term of this patent is extended or adjusted under 35 U.S.C. 154(b) by 0 days.

(21) Appl. No.: 14/689,127

(22) Filed: Apr. 17, 2015

(65) Prior Publication Data

US 2015/0297536 A1  Oct. 22, 2015

Related U.S. Application Data

(60) Provisional application No. 61/981,440, filed on Apr. 18, 2014.

(51) Int. Cl.
*A61K 31/12* (2006.01)
*A23L 33/105* (2016.01)

(52) U.S. Cl.
CPC ............ *A61K 31/12* (2013.01); *A23L 33/105* (2016.08); *A23V 2002/00* (2013.01)

(58) Field of Classification Search
None
See application file for complete search history.

(56) References Cited

U.S. PATENT DOCUMENTS

| 5,401,777 A | * | 3/1995 | Ammon | A61K 31/12 514/731 |
| 6,352,712 B1 | * | 3/2002 | Lukaczer | A23L 1/296 424/439 |

(Continued)

FOREIGN PATENT DOCUMENTS

| WO | 2005094862 | 10/2005 |
| WO | 2011056549 | 5/2011 |

(Continued)

OTHER PUBLICATIONS

Takahashi et al., Int. J. Sports Med. 2014 Published Online Oct. 28, 2013, pp. 469-475.*

(Continued)

*Primary Examiner* — Karl J Puttlitz
(74) *Attorney, Agent, or Firm* — Hamre, Schumann, Mueller & Larson, P.C.

(57) ABSTRACT

Curcumin compositions herein are described for improving muscle performance, endurance capacity and resistance to fatigue, when administered in effective amounts to a subject in need of such improvement. The compositions are comprised of curcumin and at least one pharmaceutically and/or nutraceutically acceptable excipient such as a hydrophilic carrier and exhibit enhanced bioavailability. More particularly methods are described and include use of curcumin compositions to increase exercise time, performance and capacity and to prevent muscle soreness, fatigue and injury. The compositions enhance mitochondrial biogenesis by modulating mitochondrial function, increasing mitochondrial mass and oxygen consumption, thus increasing mitochondrial aerobic capacity. The compositions reduce oxidative muscle stress, by decreasing inflammatory cytokines and inflammatory markers. Curcumin compositions are safe for consumption for pharmaceutical and/or nutraceutical purposes and are prepared by economic methods using (Continued)

conventional equipments and can be effectively used for enhancing muscle and exercise performance.

14 Claims, 6 Drawing Sheets

(56) References Cited

U.S. PATENT DOCUMENTS

| | | | |
|---|---|---|---|
| 2010/0015254 A1 | | 1/2010 | Arent |
| 2011/0034564 A1* | | 2/2011 | Parkkinen .......... A61K 36/9066 514/679 |
| 2013/0273175 A1* | | 10/2013 | Finley .................. A61K 33/34 424/635 |
| 2013/0303628 A1* | | 11/2013 | Breitenbach .......... A23L 33/105 514/679 |
| 2014/0255511 A1 | | 9/2014 | Dardevet et al. |
| 2014/0308212 A1 | | 10/2014 | Zhang |

FOREIGN PATENT DOCUMENTS

| | | | |
|---|---|---|---|
| WO | 2012156979 | * | 11/2012 |
| WO | 2014204866 | | 12/2014 |

OTHER PUBLICATIONS

Database Caplus Chemical Abstracts Service, Columbus, Ohio, US; Database Accession No. 2013:1884980, Abstract of Matsui et al., Food Style 21 (2013), 17(10), 77-78.*

Gupta et al., The AAPS Journal, vol. 15, No. 1, Jan. 2013, pp. 195-218.*

Sugawara et al., American Journal of Hypertension (2012), 25(6), 651-656.*

Tiyaboonchai et al., International Journal of Pharmaceutics 337 (2007) 299-306.*

"Dosage Forms: Non-Parenteral" in Encyclopedia of Pharmaceuticaltechnology, Sing et al., Jan. 18, 2008, pp. 749-761.*

Sasaki et al., Biol. Pharm. Bull. 34(5) 660-665 (2011).*

Kawanishi et al., Biochemical and Biophysical Research Communications 441 (2013) 573-578.*

Russell et al., "Skeletal muscle mitochondria: A major player in exercise, health and disease", Biochimica et Biophysica Acta vol. 1840, pp. 1276-1284, 2014.

Fernandez-Gonzalo et al., "Acute molecular responses in untrained and trained muscle subjected to aerobic and exercise resistance training versus resistance training alone", Acta Physiol, vol. 209, pp. 283-294, 2013.

Norrbom et al., "PGC-1α mRNA expression is influenced by metabolic perturbation in exercising human skeletal muscle", J Appl Physiol, vol. 96, pp. 189-194, 2004.

Pilegaard et al., "Transcriptional regulation of gene expression in human skeletal muscle during recovery from exercise", Am J Physiol Endocrinol Metab, vol. 279, pp. E806-E814, 2000.

Suwa et al., "The Potential Role of Sirtuins Regarding the Effects of Exercise on Aging-Related Diseases", Current Aging Science, vol. 6, pp. 178-188, 2013.

Villanova et al., "Influence of Age and Physical Exercise on Sirtuin Activity in Humans", Journal of Biological Regulators & Homeostatic Agents, vol. 27, No. 2, pp. 497-507, 2013.

Liu et al., "Curcumin Protects Neuron against Cerebral Ischemia-Induced Inflammation through Improving PPAR-Gamma Function", Evidence-Based Complementary and Alternative Medicine, vol. 2013, 10 pages, 2013 and can be found at http://www.hindawi.com/journals/ecam/2013/470975/.

Jacob et al., "Mechanism of the Anti-inflammatory Effect of Curcumin: PPAR-γ Activation", PPAR Research, vol. 2007, Article ID 89369, 5 pages, 2007.

Chung et al., "Adult Pancreatic Alpha-Cells: A New Source of Cells for Beta-Cell Regeneration", The Review of Diabetic Studies, vol. 7, No. 2, pp. 124-131, 2010.

Sharma et al., "The p38 Mitogen-Activated Protein Kinase Regulates 11β-Hydroxysteroid Dehydrogenase Type 2 (11β-HSD2) Expression in Human Trophoblast Cells through Modulation of 11 β-HSD2 Messenger Ribonucleic Acid Stability", Endocrinology, vol. 150, No. 9, pp. 4278-4286, Sep. 2009.

Heunks et al., "Xanthine oxidase is involved in exercise-induced oxidative stress in chronic obstructive pulmonary disease", Am. J. Physiol., vol. 277, pp. R1697-R1704, 1999.

Khanna et al., "α-Lipoic acid supplementation: tissue glutathione homeostasis at rest and after exercise", Am. J. Physiol., vol. 86, pp. 1191-1196, 1999.

Atalay et al., "Vitamin E regulates changes in tissue antioxidants induced by fish oil and acute exercise", Medicine & Science in Sports & Exercise, vol. 32, pp. 601-607, 2000.

Mastaloudis et al., "Endurance Exercise Results in DNA Damage as Detected by the Comet Assay", Free Radic Biol Med., pp. 966-975, 2004.

Goel et al., "Curcumin, the Golden Spice From Indian Saffron, Is a Chemosensitizer and Radiosensitizer for Tumors and Chemoprotector and Radioprotector for Normal Organs", Nutrition and Cancer, vol. 62, No. 7, pp. 919-930, 2010.

Gupta et al., "Therapeutic Roles of Curcumin: Lessons Learned from Clinical Trials", The AAPS Journal, vol. 15, No. 1, pp. 195-218, Jan. 2013.

Davis et al., "Curcumin effects on inflammation and performance recovery following eccentric exercise-induced muscle damage", Am J Physiol Regul Integr Comp Physiol., vol. 292, pp. R2168-R2173, 2007.

Takahashi et al., "Effects of Curcumin Supplementation on Exercise-Induced Oxidative Stress in Humans", Int J Sports Med, vol. 35, pp. 469-475, 2014.

Antony et al., "A pilot cross-over study to evaluate human oral bioavailability of BCM-95R CG (Biocurcumax TM), a novel bioenchanced preparation of curcumin", Indian Journal of Pharmaceutical Sciences, vol. 70, No. 4, 10 pages, 2008.

Schwerzmann et al., "Oxidative capacity of muscle and mitochondria: Correlation of physiological, biochemical, and morphometric characteristics", Proceedings of the National Academy of Sciences USA, vol. 86, pp. 1583-1587, Mar. 1989.

International Search Report and Written Opinion, issued in the corresponding International Application No. PCT/IB2015/052825, dated Nov. 9, 2015, 11 pages.

* cited by examiner

Fig. 1: Effect of Curcumin composition on PPARγ
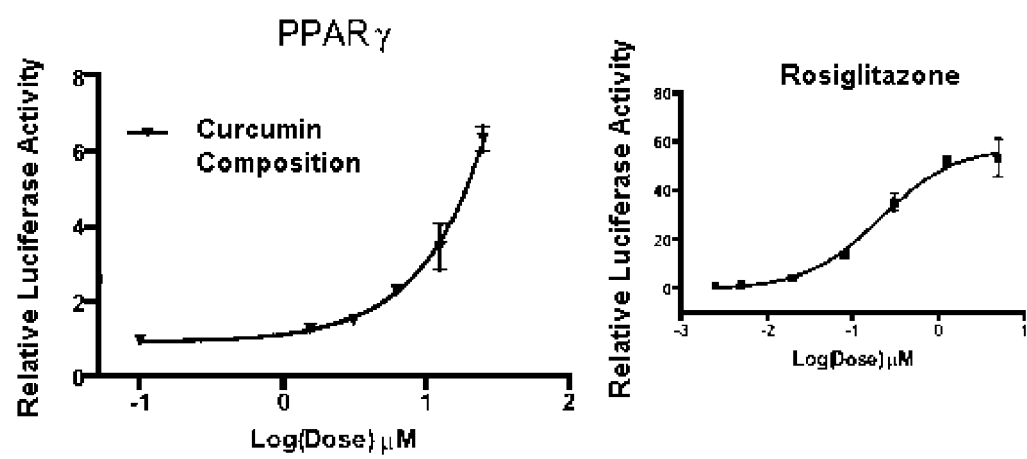
Fig. 2: Effect of Curcumin Composition on NFκB
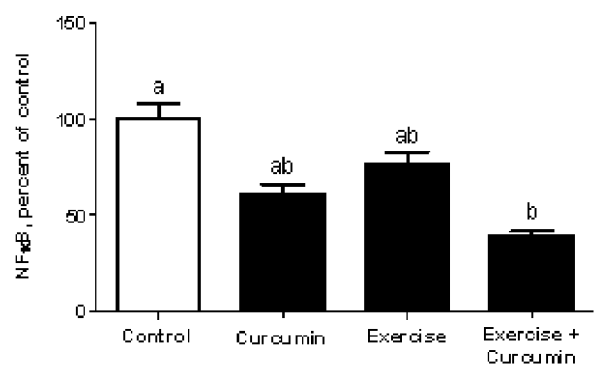

Fig. 3: Effect of Curcumin Composition on IκB
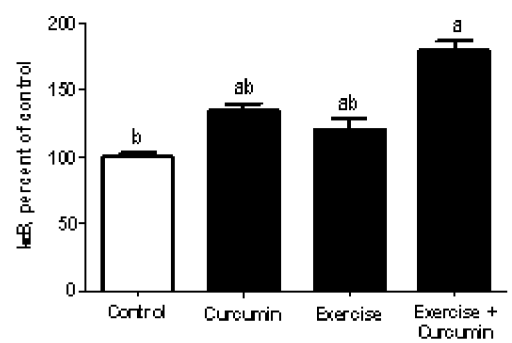
Fig. 4: Effect of Curcumin Compositions on muscle contraction
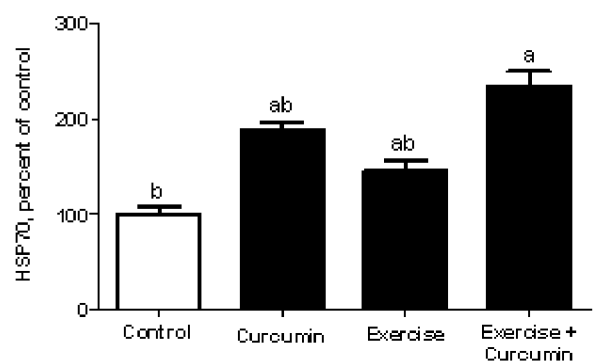

Fig. 5: Effect of Curcumin Compositions on mitochondrial gene expression
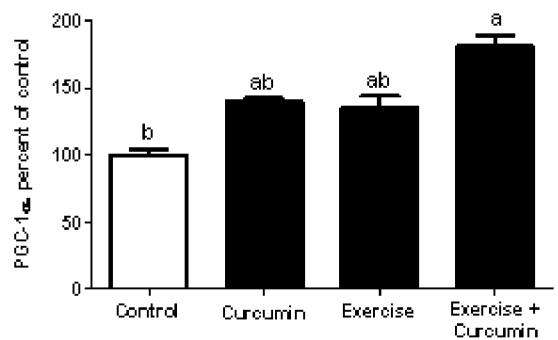
Fig. 6: Effect of curcumin compositions on Thioredoxin (TRX)
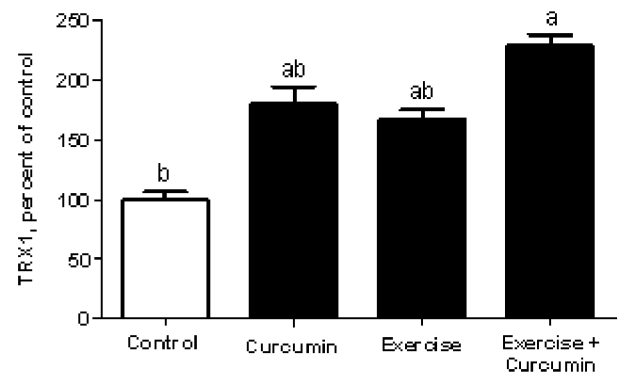

Fig. 7: Effect of Curcumin compositions on Sirtuin
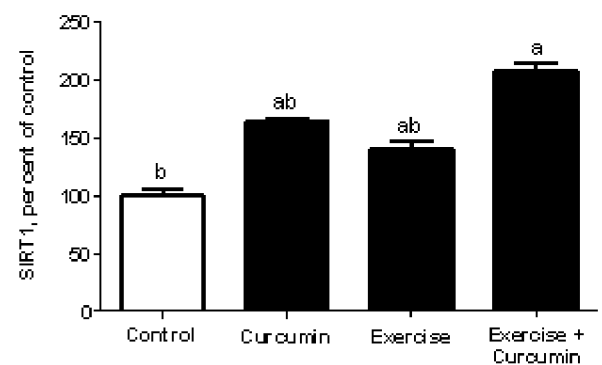
Fig. 8: Effect of Curcumin compositions on Nrf2
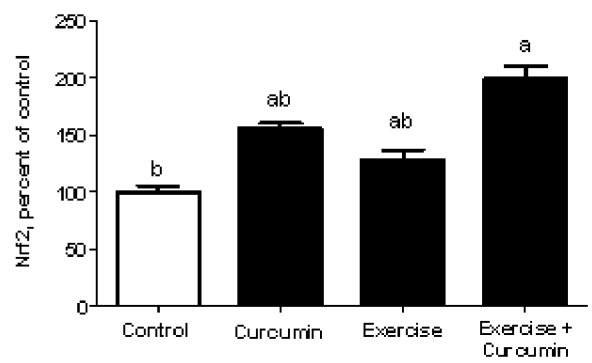

Fig. 9: Effect of Curcumin Compositions on Heme oxygenase 1
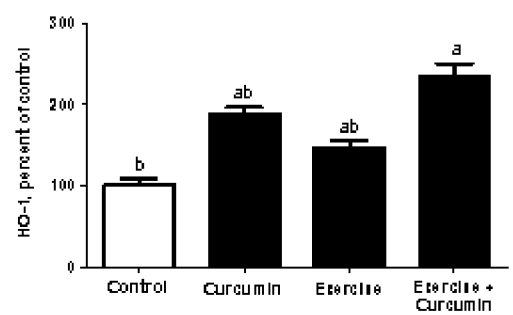
Fig. 10: Effect of Curcumin Compositions on GLUT4
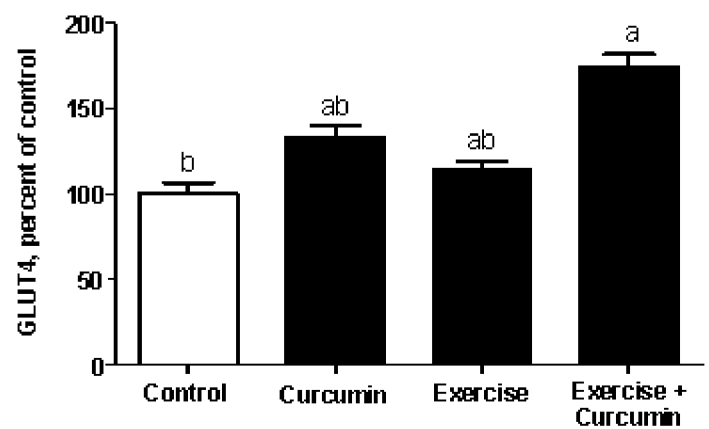

Fig. 11: Effect of Curcumin Compositions on various body markers
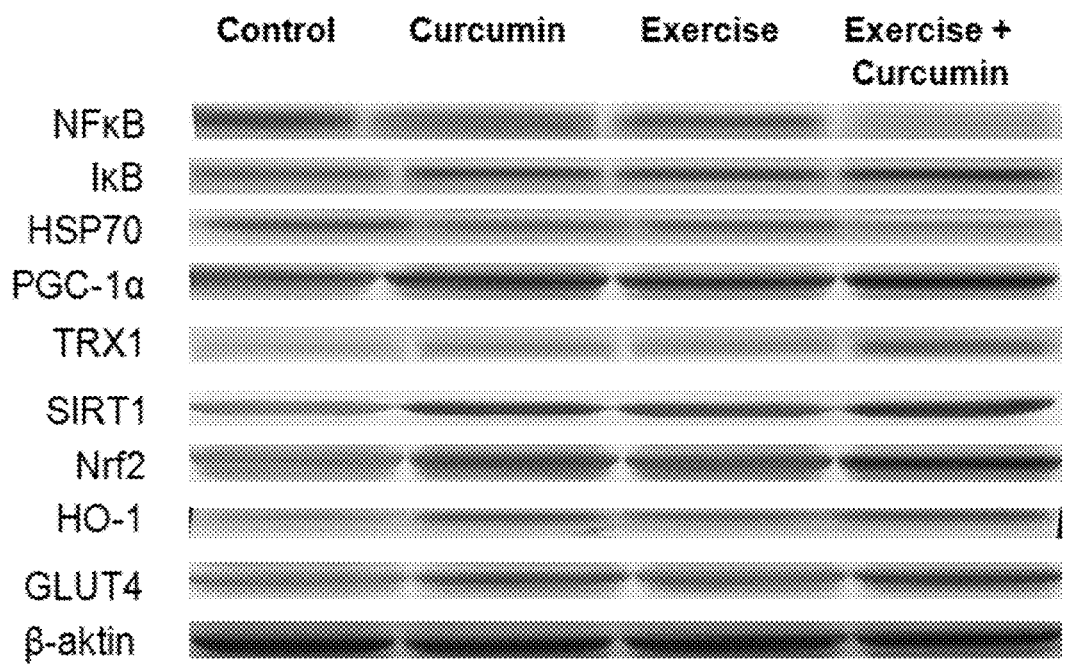

CURCUMIN COMPOSITIONS AND USES THEREOF

FIELD

Curcumin compositions herein are described to improve performance and endurance for normal physical and/or sports activities and to reduce the stress on body systems resulting from these activities. The compositions are comprised of curcumin either alone or along with at least one more excipient to form water soluble curcumin compositions having enhanced absorption. More particularly methods are described and include use of curcumin compositions to increase exercise time, endurance performance and capacity and preventing muscle soreness and exercise induced injury. Curcumin compositions and methods of treatment herein enhance endurance performance by modulating mitochondrial function, increasing mitochondrial mass and oxygen consumption, thus increasing mitochondrial aerobic capacity and enhancing oxidative capacity of the muscle. The compositions herein containing curcumin have better absorption and can improve resistance to exercise fatigue, by increasing mitochondrial energy production.

BACKGROUND

Exercise increases the utilization of oxygen in the body, and therefore enhances the production of reactive oxygen species and impairs both enzymatic and non-enzymatic antioxidant defense systems in skeletal muscle and blood. On the other hand, it has been suggested that the activity of adenosine monophosphate-activated protein kinase (AMPK) (Russel A P et al., 2014), peroxisome proliferator-activated receptor-γ coactivator 1α (PGC-1α) (Fernandez-Gonzalo et al., 2013), nuclear respiratory factor 1 (NRF1), mitochondrial transcription factor A (TFAM) (Norrbom et al., 2004; Pilegaard et al., 2000), and sirtuins (Suwa and co, 2013; Villanova et al., 2013) could play an important role in the exercise-induced adaptive response.

Sirtuin 1, silent mating type information regulation 2 homolog 1, (SIRT1) is an important regulator of metabolism which controls the activity of key transcription factors such as PGC-1α, forkhead box protein O1 (FOXO1), and p53, which play a key role in the training response. Therefore, activators of SIRT1, have potentially beneficial effects which enhance aerobic performance. Curcumin was a potent peroxisome proliferator-activated receptor gamma (PPAR γ) agonist in that it up regulated PPAR γ expression and PPAR γ-peroxisome proliferator response element (PPRE) binding activity (Liu et al., 2013; Jacob et al., 2007). Curcumin may regulate molecules involved in energy homeostasis. SIRT1 is known to deacetylate histones and non-histone proteins including transcription factors thereby regulating metabolism, stress resistance, cellular survival, cellular senescence/aging, inflammation-immune function, endothelial functions, and circadian rhythms. Curcumin has antioxidant and anti-inflammatory properties via modulating different pathways, such as nuclear factor kappa light chain enhancer of activated B cells (NF-κB) and mitogen activated protein kinase (MAPK)-dependent signaling pathways (Chung et al., 2010; Sharma et al., 2009).

Recent studies have indicated that antioxidant supplementation led to the prevention of strenuous exercise induced oxidative injury in in-vivo studies. Many studies have indicated that antioxidant nutrient supplementations prevented strenuous exercise-induced oxidative injury in human subjects and rats (Heunks, L. M et al., Xanthine oxidase is involved in exercise induced oxidative stress in chronic obstructive pulmonary disease. Am. J. Physiol., 1999; 277, R1697-R1704; Khanna, S., Atalay, M., Laaksonen, D. E., Gul, M., Roy, S., & Sen, C. K. (1999). Alpha-lipoic acid supplementation: Tissue glutathione homeostasis at rest and after exercise. Journal of Applied Physiology, 86, 1191-1196.

Atalay, M., Laaksonen, D. E., Khanna, S., Kaliste-Korhonen, E., Hanninen, O., and Sen, C. K. (2000) Vitamin E regulates changes in tissue antioxidants induced by fish oil and acute exercise. Medicine and Science in Sports and Exercise 32, 601-607; Mastaloudis A, et al. Endurance exercise results in DNA damage as detected by the comet assay. Free Radic Biol Med. 2004).

Curcumin (1,7-bis(4-hydroxy 3-methoxy phenyl)-1,6-heptadiene-3,5-dione), a polyphenolic compound isolated from *Curcuma longa* L. and present in curry spice, has a long story of use in Indian medicine for anti-inflammatory and other therapeutic purposes (Goel and Aggarwal, 2010). It has exhibited antioxidant, anticarcinogenic, hepatoprotective, thrombosuppressive, cardioprotective, anti-arthritic, and anti-infectious properties (Gupta et al., 2013). The curcuminoids, curcumin, bisdemethoxy curcumin, demethoxy curcumin and tetrahydro curcumin are major constituents of the curcumin formulation derived from the extraction process.

Downhill running is associated with fiber damage, inflammation, delayed-onset muscle soreness, and various functional deficits. Curcumin, has been investigated for its anti-inflammatory activity and may offset some of the damage and functional deficits associated with downhill running Davis J M, et al 2007, examined the effects of curcumin on inflammation and recovery of running performance following downhill running in mice. It was found that downhill running was associated with an increase in inflammatory cytokines and creatine kinase that were blunted by curcumin feedings. These results support the hypothesis that curcumin can reduce inflammation and offset some of the performance deficits associated with eccentric exercise-induced muscle damage.

Takahashi M et al. Int J Sports Med. 2014, investigated the effects of curcumin supplementation on exercise-induced oxidative stress in humans. Each participant received oral administration of 90 mg of curcumin or the placebo 2 h before exercise and immediately after exercise. Serum biological antioxidant potential concentrations measured immediately after exercise were significantly elevated in the single and double curcumin supplementation trials compared with pre-exercise values. These findings indicate that curcumin supplementation can attenuate exercise-induced oxidative stress by increasing blood antioxidant capacity.

WO 2011056549 describes dietary supplement compositions that include an adaptogenic agent, an anti-inflammation agent, and an anti-oxidant. Methods for using dietary supplement compositions include (i) inhibiting, decreasing, and/or preventing delayed onset of muscle soreness (DOMS); (ii) inhibiting, decreasing, and/or preventing exercise-induced muscle damage; and/or (iii) modulating the expression of genes that are correlated with exercise-induced muscle damage.

WO2014204866A1 describes mixtures of prenylated flavonoids, stilbenes, or both with flavans or curcuminoids which are capable of modulating joint inflammation, joint pain, joint stiffness, cartilage degradation, or improving mobility, range of motion, flexibility, joint physical function, or any combination thereof. Such a mixture of compounds can optionally be used in combination with other joint management agents, such as non-steroidal anti-inflammatory agents/analgesics, cyclooxygenase/lipoxygenase COX/LOX inhibiting agents, glucosamine compounds, neuropathic pain relief agents and the like.

Patent application US20140308212A1 relates to a composition, comprising a therapeutic agent such as curcumin encapsulated by a microvesicle, wherein the microvesicle is derived from an edible plant. When such compositions are administered amount of inflammatory cytokine in a subject is reduced to considerable level.

US20140255511A1 relates to a method for treatment or prevention of muscle atrophy caused by immobilization comprising administering a composition comprising leucine, isoleucine, valine and at least one antioxidant such as curcumin.

SUMMARY

Although references as above relate to curcumin compositions for use as an anti-inflammatory or for reducing oxidative stress, there is no teaching about methods of administering curcumin compositions for modulating mitochondrial function and enhancing oxidative capacity of the muscles, thus providing adequate protection against muscle degeneration and to enhance stamina or endurance during exercise.

Applicant of the present application has carried out rigorous experimentation for optimizing compositions comprising curcumin alone or in combination with at least one more excipient and its evaluation as sports nutrition through exhaustive in-vitro and in-vivo trials to demonstrate use of curcumin compositions for increasing exercise time, endurance capacity and preventing exercise induced muscle soreness and injury.

Compositions comprising curcumin as described herein can be effective in significantly overcoming the exhaustive exercise-induced oxidative stress and muscle injury, and can be administered to subjects in need. Such subjects include, for example animals, including mammalian subjects and may be administered to human subjects. Curcumin compositions described herein are found to favorably modulate mitochondrial function and significantly affect mitochondrial biogenesis in myoblast cell lines, modify serum parameters, antioxidant status of muscle in rats after exhaustive exercise. In addition, curcumin composition favorably modified NF-kB, nuclear respiratory factor-2/heme oxygenase-1 (Nrf2/HO-1) and SIRT1 pathways in the skeletal muscle of exercise-trained and sedentary rats.

Curcumin compositions described herein are comprised of curcumin alone and/or formulated with at least one excipient. The compositions may be in the form of curcumin extract or may be formulated using suitable excipients to prepare convenient dosage forms. At least one excipient may be selected from the group of, but not limited to a hydrophilic carrier, a fat, an antioxidant, diluents, stabilizer, surfactant and the like or the combination thereof, which are acceptable for pharmaceutical or nutraceutical formulations. These compositions can be useful in significantly modulating mitochondrial biogenesis, enhancing oxidative capacity of muscles, increasing exercise time, endurance capacity and preventing exercise induced muscle soreness and injury, when administered in effective amounts. The compositions herein can be also useful for activating PPARγ receptors, decreasing inflammatory markers, altering antioxidant stress and improving cardio metabolic markers in the presence and absence of exercise.

The compositions containing curcumin as described herein can be useful and safe for humans without any or significant side effects and methods of use are herein described for application to improve physical activities, exercise performance and exercise endurance along with decreasing the fatigue. Curcumin compositions and methods of use administering the composition as described herein have been developed based on findings that when curcumin is combined with at least one pharmaceutically and/or nutraceutically acceptable excipient or the combination thereof, the bioavailability of curcumin is surprisingly enhanced. Such a combination resulting in enhanced bioavailability is useful for increasing exercise time, endurance capacity and preventing or limiting exercise induced injury.

BRIEF DESCRIPTION OF THE DRAWINGS

FIG. 1: Effect of Curcumin composition on peroxisome proliferator-activated receptor gamma (PPARγ).

FIG. 2: Effect of Curcumin Composition on nuclear factor kappa beta (NFκB).

FIG. 3: Effect of Curcumin Composition on IκB (nuclear factor of kappa light polypeptide gene enhancer in B-cells inhibitor).

FIG. 4: Effect of Curcumin Compositions on muscle contraction.

FIG. 5: Effect of Curcumin Compositions on mitochondrial gene expression.

FIG. 6: Effect of curcumin compositions on thioredoxin (TRX).

FIG. 7: Effect of Curcumin compositions on sirtuin.

FIG. 8: Effect of Curcumin compositions on nuclear factor erythroid 2-related factor (Nrf2).

FIG. 9: Effect of Curcumin Compositions on heme oxygenase 1 (HO-1).

FIG. 10: Effect of Curcumin Compositions on glucose transporter type 4 (GLUT4).

FIG. 11: Effect of Curcumin Compositions on various body markers.

DETAILED DESCRIPTION

Curcumin [1,7-bis(4-hydroxy-3-methoxyphenyl)-1,6-heptadien-3,5-dione] is a hydrophobic polyphenol derivative which is a potent antioxidant and may be derived from the spice turmeric. Commercial curcumin can sometimes contain approximately, 77% diferuloylmethane, 17% demethoxycurcumin, and 6% bisdemethoxycurcumin. Curcumin is a major active ingredient of *Curcuma Longa*. *Curcuma longa* (turmeric) is a well-known indigenous herbal medicine. It is known for its diverse biological actions and pharmacological activities including anti-inflammatory, antioxidant, antiproliferative, antimicrobial, anticarcinogenic and antiangiogenic properties.

It is to be appreciated that the term curcumin can be interpreted to be within the scope of the term curcuminoids, which can in general include components curcumin, methoxy curcumin, demethoxy curcumin and bisdemethoxy curcumin. Commercial products which may be referred to as "curcumin" may have these three components, along with other components belonging to the class curcuminoids It is also to be appreciated that diarylheptanoid are considered a class of compounds to which curcuminoids (e.g. curcumin) belongs. Other similar Diarylheptanoids, such as those that may be obtained from ginger may possess similar properties as curcuminoids (e.g. curcumin). It will be appreciated that while curcuminoids (e.g. curcumin) may be described in detail herein, it will be appreciated that other diarylheptanoids may have similar or the same biological properties and effects, and which may be included in such compositions as described herein and may be used in the methods of treatment as described herein.

The beneficial effects of curcumin have been well known. However, there are many problems associated with the bioavailability of curcumin when delivered in the oral form. A majority of ingested curcumin is excreted through the feces unmetabolized and the minority that gets absorbed is converted into other metabolites and excreted. Curcumin does not easily penetrate the gastrointestinal tract and is subject to liver and other intestinal enzymes. Owing to these enzymes, the curcumin within the body is rapidly metabolised thus reducing its bioavailability in the body. The small amount of curcumin that enters the bloodstream is rapidly metabolized by the liver and kidney. Therefore, although curcumin is highly lipophilic (and so easily crosses the blood brain harrier), only very small amounts of orally administered curcumin are detected in the serum and in the brain tissue.

Cytochrome P450 is a phase I metabolizing isoenzyme which is required for metabolizing toxic chemicals such as heterocyclic amines to induce DNA adduct formation leading to carcinogenesis. Curcumin when ingested in the body enters the gastrointestinal tract and is found to inhibit Cytochrome P450. There have been studies carried out to increase the bioavailability of curcumin when used along with piperine. Piperine is a bioenhancer which inhibits Cytochrome P450 and thereby prevents metabolism of curcumin in the body. The compositions described herein are seen to enhance the bioavailability without the presence of any additional bioenhancer.

Curcumin compositions described herein are comprised of either curcumin alone or in combination with at least one or more pharmaceutically and/or nutraceutically acceptable excipients to increase water solubility and absorption of curcumin. More preferably, curcumin composition is formulated using excipients selected from the group of, but not limited to a hydrophilic carrier, cellulosic polymers, solubilizers, stabilizers, emulsifiers, fats, diluents, binder, antioxidants, and the like or the combinations thereof. When curcumin is combined with at least one pharmaceutically or nutraceutically acceptable excipient such as a hydrophilic carrier and formulated as a solid dispersion of curcumin by adding other excipients, the bioavailability of such optimized curcumin formulation is enhanced.

Curcumin compositions, as described herein are also comprised of curcumin and at least one excipient such as hydrophilic carrier, which can be formulated as spray dried free flowing soluble granules.

In some embodiments, a process for the preparation of a curcumin composition having enhanced bioavailability suitable for increasing exercise time, endurance capacity and/or preventing or limiting exercise induced injury comprises: (i) dissolving curcumin, at least one excipient such as hydrophilic carrier and adding other excipients such as a fat and an antioxidant, in a solvent to form a homogenous mass; (ii) warming the resultant mass at a temperature ranging from 25° C. to 60° C. for a period of about 4 to 8 hours to obtain a dry wet mass; (iii) removing the solvent by evaporation to form a dry mass; and (iv) pulverizing the dry mass to form a fine powder.

In some embodiments, the process for preparation of soluble granules of curcumin is described, wherein curcumin is dispersed in solid hydrophilic carrier along with at least one more pharmaceutical or nutraceutical excipient in suitable organic solvent, which is safe for human consumption and spray dried to get the product. This product is also called as Ultrasol dry nutrient system. These granules can be filled in sachets as one of the convenient way for administration or can be suspended in suitable oil medium with stirring and followed by milling to get uniform suspension.

As per one more embodiment, curcumin used in the step (i) can be commercially available with an assay ranging between about 85-96%. It can also be an extract of turmeric rich in curcumin. The amount of curcumin added may be sufficient to produce a water soluble curcumin with an assay of 1-55% curcumin. These percentages refer to total curcuminoids (e.g. chemical constituents present in turmeric). It will be appreciated that as curcumin is one of the principle curcuminoids present in turmeric and present in major amounts, reference is made to curcumin in common instead of curcuminoids, although other curcuminoids such as demethoxy curcumin and bisdemethoxy curcumin are present in lesser amounts along with curcumin in turmeric, and are included in the percentages and part of the curcumin compositions described herein.

In one more embodiment, the solid hydrophilic carrier employed in preparation of curcumin compositions is selected from the group such as, but not limited to, cellulose derivatives, polyacrylates, polyethylene glycols, povidones, starch and starch derivatives, gums, sugars, and the like.

According to one important embodiment, the hydrophilic carrier used in the step (i) can be selected from soluble starch, hydroxy propyl methyl cellulose, sodium carboxy methyl cellulose, polyvinyl pyrrolidone, polyethylene glycols 200-20000, glycerol, sorbitol, mannitol, glucose, sugar, and mixtures thereof. The quantity of hydrophilic carrier added may range between 10-90%. The above percentage refers to weight percentage of the hydrophilic carrier with respect to the weight of the total composition, thus weight by weight percentage.

As per one embodiment the fat used in the step (i) may be selected from milk fat, medium chain triglycerides, long chain triglycerides, hydrogenated vegetable oils, and mixtures thereof. The quantity of fat used may range from 1-25%. The above percentage refers to weight percentage of the fat with respect to the weight of the total composition, thus weight by weight percentage.

As per one more embodiment, at least one more excipient employed in the composition may be selected from, but not limited to diluents, binder, surfactant, solubilizer, antioxidant, solvent and the like or the combinations thereof. The antioxidants used in step (i) can be selected from natural tocopherols, ascorbyl palmitate, rosemary extract, epigallocatechin gallate, catechins, ascorbic acid, and mixtures thereof. The amount of antioxidant used may range between 1-10%. The above percentage refers to weight percentage of the antioxidant with respect to the weight of the total composition, thus weight by weight percentage.

The solvent used for dissolving in the step (i) may be selected from isopropyl alcohol, acetone, methanol, alcohol, and mixtures thereof. The temperature maintained for obtaining an homogenous mass may range from ambient to 70° C.; preferably 25° C. to 60° C.

The removal of solvent in step (ii) can be performed in vacuum distillation or evaporation technique, or by spray drying technique. The resultant dry mass is pulverized by using, for example, mortar and pestle, mixer-grinder, multimill, ball mill, jet mill and the like.

The compositions may comprise curcumin, a hydrophilic carrier, a fat and at least one more excipient such as an antioxidant. The antioxidant along with curcumin can inhibit the Cytochrome P450. On the other hand, the presence of fat coating on the composition can prevent the composition from attack by liver microsomal or other intestinal enzymes as these enzymes attack only aqueous compounds. Thus, the antioxidant and the fat can enhance the bioavailability of curcumin.

Applicant of the present application has evaluated curcumin compositions in muscle cells and in exercise induced/ sedentary rodents to evaluate the effect on exercise pattern and endurance performance, which is nowhere reported in prior art. Co-relation between mitochondrial biogenesis and physical activity and/or exercise is well known.

Curcumin compositions described herein, may be administered in effective amounts, to a subject in need thereof, for enhancing muscle performance, endurance activity, increasing exercise time and reducing fatigue and muscle injury, in effective amounts.

Term subject may relate to "a subject desiring this improvement such as a mammal, selected from a group of, but not limited to an animal, a human being such as an athlete, a non-athlete, performing normal physical activities, sports, exercise and/or the combination thereof". The compositions may be administered, such as for example on an activity day, or for a prolonged period of time, or for a week duration, as per the need in effective amounts such as 0.002 mg to 20 gm/kg body weight of a subject. The duration of administration in doses mentioned as above or lower or higher will depend on the need of improvement of the condition in subject under consideration.

Mitochondria represent the principal energy source in cells, converting nutrients to energy via cellular respiration. The function and content of mitochondria increase with physical training, aerobic and/or anaerobic exercise and decrease with physical inactivity.

While anaerobic exercise is primarily concerned with strength, aerobic exercise focuses on endurance. Both are important types of exercise and both stimulate an increase in mitochondria. However, aerobic exercise leads to a greater concentration. An alteration in the rate of oxygen consumption can serve as a useful indicator of mitochondrial dysfunction. By measuring oxygen consumption, a direct and specific assessment of the functioning of the electron transport chain (the key element of oxidative phosphorylation and cellular metabolism) may be obtained. Mitochondrial abundance (mass) can also be used as an indicator of mitochondrial biogenesis.

During endurance training, various adaptational changes occur in several tissues. In skeletal muscle, fatty acid usage is enhanced and mitochondrial content and activity are increased. The transcriptional coactivator peroxisome proliferator-activated receptor gamma coactivator 1α (PGC-1α) plays a key role in the regulation of mitochondrial biogenesis and function. During exercise, increased energy demands induce PGC-1α expression to answer cellular energy needs. It has been shown that during exercise, PGC-1α coordinately increases mitochondrial biogenesis and respiration rates in skeletal muscle as well as the uptake and utilization of substrates for energy production. In some embodiments, the curcumin compositions and methods of treatment administering the composition as described herein can significantly alter the serum metabolic and inflammatory parameters and antioxidant status and inflammatory markers of muscle in rats after exhaustive exercise and/or without exercise.

Significant effects of curcumin compositions on muscle proteins and on exercise endurance performance are due to its increased solubility and enhanced bioavailability. For example, the solubility was enhanced by dispersing a highly purified powder [e.g. with min 95% curcuminoids] in a water-soluble carrier (e.g. polyvinyl pyrrolidone) along with other excipients, such as fat and an antioxidant. Stabilizers, such as for example tocopherol and ascorbyl palmitate were used to prevent degradation of curcumin Curcumin compositions described herein exhibit enhanced bioavailability and the compositions can be available in orally administrable solid, semisolid, liquid forms, selected from, but not limited to dosages such as, powders, granules, pellets, beadlets, caplets, tablets, capsules, soft gel capsules, solution, emulsions, suspensions, oil suspensions, dispersions, and the like.

Curcumin compositions described herein are evaluated for their effects on sports nutrition biomarkers in undifferentiated myoblasts to study their effect on mitochondrial oxygen consumption, mitochondrial mass, and PGC-1α expression and on overall mitochondrial biogenesis.

Curcumin compositions described herein and methods of using it were also evaluated for effectiveness in significantly overcoming the exhaustive exercise-induced oxidative stress. The compositions were checked for their effect on serum metabolic and inflammatory parameters and antioxidant status and inflammatory markers of muscle in rats after exhaustive exercise and/or without exercise. In addition, the effect of the curcumin composition was also evaluated on NF-kB, nuclear respiratory factor-2/heme oxygenase-1 (Nrf2/HO-1) and SIRT1 pathways in the skeletal muscle of exercise-trained and sedentary rats.

The Examples given below are provided to illustrate the water soluble compositions of curcumin and uses thereof. While the compositions and methods have been described in terms of illustrative embodiments, certain modifications and equivalents will be apparent to those skilled in the art and are intended to be included within the scope of the compositions and methods herein. The details and advantages of which are explained hereunder in greater detail in relation to non-limiting exemplary illustrations.

EXAMPLES

A. Preparation of Curcumin Compositions

Example 1

18 g of curcumin (95%), 0.75 g of ascorbyl palmitate, 1.1 g of Green tea extract containing 0.55 g of EGCG (epigallocatechin gallate), 0.8 G of natural tocopherol, 10 g of HPMC (hydroxypropyl methyl cellulose), 265 g of polyvinyl pyrrolidone (K 30) and 30 g of Medium Chain Triglyceride were suspended in 600 g of isopropyl alcohol to obtain a homogenous mass. The resultant homogenous mass was then heated to 70° C. to obtain a dry wet mass which was then subjected to distillation under the reduced pressure 600 mm Hg for removing isopropyl alcohol to obtain a dry mass. The dried mass was then pulverized in a mixer-grinder to form a fine yellow water-soluble powder containing 5.8% of curcumin.

Example 2

72 g of curcumin (95%), 8 g of natural tocopherol, 6 g of ascorbyl palmitate, 18 g of hydroxypropyl methyl cellulose, 15 g of hydrogenated soybean oil, and 200 g of mannitol were suspended in 500 g of ethyl alcohol to obtain a mixture. The mixture was then homogenized and heated at 60° C. to obtain a homogenized mass. This homogenized mass was subjected to evaporation under vacuum for removing ethyl alcohol to yield 317 g of dried mass. The resultant dry mass was then pulverized in a mortar with a pestle to yield a yellow powder with 20.1% curcumin.

Example 3

275 g of curcumin (95%), 5 g of Green tea Extract containing 50% EGCG, 10 g of ascorbyl palmitate, 30 g of Medium Chain Triglyceride, 20 g of hydrogenated soybean oil, and 175 g of Polyvinyl pyrrolidone were suspended in 500 g of ethyl alcohol. The mixture was homogenized and heated at 60° C. The resultant mixture is then subjected to evaporation under vacuum for removing ethyl alcohol to yield 520 g of dried mass. The resultant dried mass was then pulverized in a mortar with a pestle to yield a yellow powder with 51.3% curcumin.

Example 4

274 g of curcumin (95%), 5.1 g of Green tea Extract containing 50% EGCG, 10.6 g of ascorbyl palmitate, 31 g of Medium Chain Triglyceride, 20 g of hydrogenated soybean oil, and 175 g of Polyethylene Glycol 6000 were suspended in 500 g of acetone. The mixture was homogenized and heated at 55° C. to obtain a homogenized mass. The resultant mixture was subjected to evaporation of acetone under vacuum to yield 523 g of dried mass. The mass was then pulverized in a mortar with a pestle to yield a yellow powder with 50.6% curcumin.

B. Evaluation of Curcumin Compositions

Curcumin compositions that are capable of increasing exercise time, endurance capacity, and that can prevent and/or reduce exercise induced injury were subjected to the following tests to demonstrate its efficacy.

Example 5

In-Vitro Screens for Sports Nutrition Biomarkers in C2C12 Cells

C2C12 cells (ATCC® CRL-1772) were seeded in 24- or 96-well culture plates as undifferentiated myoblasts and grown to 100% confluency in ATCC-formulated Dulbecco's Modified Eagle's Medium (DMEM) supplemented with 10% heat-inactivated fetal bovine serum (FBS). Upon reaching confluency, cells were induced to differentiate from myoblasts into multinucleated, fused myotubes, which exhibit similar characteristics to mature muscle cells. Differentiation medium consisted of ATCC-formulated DMEM supplemented with 2% heat-inactivated horse serum and was changed daily during the differentiation process. Cell culture conditions were maintained at 37° C. in a humidified atmosphere of 5% $CO_2$/95% air. After 5 days of differentiation, cells were incubated in the presence or absence of a series of test inputs and controls. A range of test input dosages were assessed. The effect of select test inputs was assessed using the following assays:

a. Cell Viability Measurement

In order to determine appropriate test input dosages for endurance/stamina related assays, differentiated C2C12 myotubes were treated with a range of test input concentrations. Cell viability was assessed by MTT (3-(4,5-desethyithiazol-2-yl)-2,5-diphenyl-tetrazolium bromide) assay, a common measurement of the in vitro cytotoxicity of test inputs. Conversion of MTT reagent (yellow colour) to formazan (purple colour) by living cells provides an indication of mitochondrial activity, which is directly related to cell viability. C2C12 cells were seeded in 96-well culture plates at a density of $2 \times 10^4$ cells/mL and induced to differentiate. After a 24-hour pre-treatment with a range of select test input concentrations, used medium was removed, replaced with MTT labeling reagent (5 mg/mL in phosphate buffered saline), and incubated for 4 hours. The purple coloured formazan crystals formed in the intact cells were then dissolved overnight with MTT solubilisation solution (10% SDS in 0.01 M HCl). After solubilisation of the formazan crystals, absorbance was measured at 570 nm with a microplate reader. Data obtained from this cytotoxicity testing allowed for dose range optimization of the test inputs for further testing.

b. Mitochondrial Oxygen Consumption:

Extracellular oxygen consumption in differentiated C2C12 cells was measured by assessing phosphorescence of a porphyrin-based, water soluble, oxygen sensitive probe (MitoXpress®-Xtra-HS, Luxcel Biosciences). Probe fluorescence is quenched by molecular oxygen ($O_2$), resulting in lower probe signal. As cellular respiration reduces the concentration of $O_2$, probe signal increases. The rate of this increase is related to the rate of cellular oxygen consumption. C2C12 cells were seeded in 96-well culture plates at a density of $2 \times 10^4$ cells/mL, induced to differentiate, and incubated with MitoXpressprobe (1 µM), in the presence or absence of the curcumin composition (10 ug/ml). High sensitivity mineral oil was added (100 µL/well) to increase assay sensitivity by minimizing interference from ambient $O_2$. Probe fluorescence was measured (excitation 380 nm, emission 645 nm) using a fluorescence plate reader.

c. Mitochondrial Mass:

The effect of treatment with curcumin composition (10 ug/ml) on mitochondrial mass was assessed by measuring changes in fluorescent intensity in differentiated C2C12 cells. The nonylacridine orange (NAO) probe binds to cardiolipin in all mitochondria, regardless of their energetic state, providing a measure of mitochondrial mass and an indication of mitochondrial biogenesis. C2C12 cells were seeded in 96-well culture plates at a density of $2 \times 10^4$ cells/mL, induced to differentiate, and pre-treated with or without select test inputs and controls. Following treatment, media was replaced with NAO probe (100 ng/mL) and incubated for 30 mins at 37° C. in a humidified atmosphere of 5% $CO_2$/95% air. Probe fluorescence was measured (excitation 380 nm, emission 645 nm) using a fluorescence plate reader. Fluorescent intensity relative to untreated control was then calculated. To standardize probe fluorescence to protein content of the cells, total protein content (in µg) was assessed by bicinchoninic acid (BCA) using bovine serum albumin as standard.

d. PGC-1α Expression

To evaluate the effect of treatment with curcumin on PGC1α synthesis in differentiated C2C12 cells, the mouse PGC1α enzyme-linked immunosorbent assay (ELISA) kit (My BioSource) was utilized. The kit provides a quantitative measurement of mouse PGC1α concentrations in cell culture supernatants by employing an antibody specific coated 96-well plate. Standards and samples were added to the coated plate and any PGC1α present in the sample bound to the immobilized antibody. After removing any unbound antibody, a biotin-conjugated antibody specific for PGC1α was added to the wells. Then horseradish peroxidase (HRP)-conjugated streptavidin was added to the wells. The wells were washed again, followed by addition of a colorimetric substrate solution. Color developed in proportion to the amount of bound PGC1α. Then the color intensity was read at Absorbance 450 nm using a microplate reader. Blank-corrected unknown sample protein concentrations were then extrapolated from a known standard curve.

Example 6

In-Vivo Evaluation of Curcumin Compositions in Rodents

Thirty-eight male Wistar rats (age: 8 week, weight: 180±20 g) were housed in a controlled environment with a 12:12-hour (h) light-dark cycle at 22° C. and were provided with rat chow and water ad libitum. All experiments were conducted under the National Institutes of Health's Guidelines for the Care and Use of Laboratory Animals and approved by the Ethics Committee of the Veterinary Control Institute.

Animals were randomly divided into the following four groups: (i) control [no exercise] (C); (ii) control diet+curcumin treatment [no exercise]; (iii) control diet+subjected to physical exercise; and (iv) control diet+subjected to physical exercise and curcumin treatment (ES).

Composition containing Curcumin 100 mg/kg (contains approximately 20 mg of curcuminoids) was administered daily as an oral supplement per day for 6 weeks.

It will be appreciated that a dose of 100 mg/kg of the water soluble composition containing curcumin, which contains approximately 20 mg of curcuminoids is one example only of a dosage for the general compositions described herein and compositions which may be administered in the methods of treatment described herein. In some embodiments, for example when the dosage is 100 mg/kg, the remaining 80 mg may include about 65-70 mg of one or more hydrophilic carriers, such as for example polyvinyl pyrrolidone, about 4-8 mg of one or more antioxidants, such as for example limonene and/or ascorbyl palmitate, and about 4-8 mg of one or more fats, such as for example tocopherol. It is to be appreciated that these relative amounts and examples are not meant to be limiting as other suitable amounts may be used within a 100 mg/kg dosage or within other dosages, and are not meant to be limiting as other examples may be used for the hydrophilic carrier, the antioxidant, and the fat, and may include other components.

It is to be appreciated that the term curcumin can interpreted to be within the scope of the term curcuminoids, which can in general include components curcumin, methoxy curcumin, demethoxy curcumin and bisdemethoxy curcumin. Commercial products which may be referred to as "curcumin" may have these components. It will be appreciated that the term curcumin composition as used herein includes all curcuminoids, including curcumin, methoxy curcumin, demethoxy curcumin and bisdemethoxy curcumin.

It is also to be appreciated that diarylheptanoid are considered a class of compounds to which curcuminoids (e.g. curcumin) belongs. Other diarylheptanoids, such as those that may be obtained from ginger may possess similar properties as curcuminoids (e.g. curcumin). It will be appreciated that while curcuminoids (e.g. curcumin) may be described in detail herein, it will be appreciated that other diarylheptanoids may have similar or the same biological properties and effects, and which may be included in such compositions as described herein and may be used in the methods of treatment as described herein.

The following parameters were measured, AMP-activated protein kinase (AMPK), peroxisome proliferator-activated receptor-γ coactivator 1α (PGC-1α) (increase aerobic performance), nuclear respiratory factor 1 (NRF1) mitochondrial transcription factor A (TFAM) and sirtuins. These parameters are suggested to play an important role in the exercise-induced adaptive response.

SIRT1 is an important regulator of metabolism. SIRT1 controls the activity of key transcription factors such as PGC-1α, FOXO1, and p53.

Inflammatory markers can include such as for example lactate dehydrogenase (LDH), creatine kinase (CK) & Lactate. Curcumin decreases the level of these inflammatory markers.

The levels of antioxidant enzymes such as muscle malondialdehyde (MDA), superoxide dismutase (SOD), glutathione peroxidase (GPx), and glutathione (GSH) is evaluated in the study.

Curcumin activates PPARγ (peroxisome proliferator-activated receptor gamma) receptors which are essential for regulating fatty acid storage and glucose metabolism. The genes activated by PPARγ further stimulate lipid uptake and adipogenesis by fat cells.

Results:
1. In-Vitro Evaluation in C2C12 Cells
  a. Mitochondrial Oxygen Consumption:

Curcumin compositions herein at 10 ug/ml induced an increase of 18% in mitochondrial oxygen consumption. These results suggest that a water soluble curcumin composition has a significant effect on mitochondrial oxygen consumption (Table 1). The results reported below are consistent with findings related to Examples 1 to 4, and in particular Example 2.

TABLE 1

Effect of curcumin composition on Mitochondrial Oxygen Consumption

| Sample | Average fluorescent intensity | SEM | Average relative to control |
|---|---|---|---|
| Control (non treated cells) | 29.56 | 0.37 | 99.87 |
| Curcumin composition | 34.96 | 0.23 | 118.10 | b. Mitochondrial Mass:

Curcumin compositions, as described herein induced an increase of 14.41% in mitochondrial mass at 10 ug/ml.

TABLE 2

Effect of curcumin composition on Mitochondrial mass

| Sample | Average Fluorescent Intensity | SEM | Average relative to control |
|---|---|---|---|
| Control (non treated cells) | 13715.89 | 28.31 | 100.00 |
| Curcumin composition | 15691.89 | 538.38 | 114.41 | c. PGC-1α Expression

Treatment of the C2 C12 muscle cells with Curcumin compositions at 10 ug/ml significantly increased the expression of PGC1α, suggesting an increase in mitochondrial biogenesis.

TABLE 3

Effect of curcumin composition on PGC1α expression

| Sample | Average-PGC1α concentration (pg/ml) | SEM | % increase relative to control |
|---|---|---|---|
| Control (non-treated cells) | 33.72 | 3.89 | 100.00 |
| Curcumin composition | 51.87 | 3.42 | 153.8 | d. Effect of Curcumin Composition on PPARγ

The water soluble compositions containing curcumin (curcumin composition) described herein can significantly activate PPARγ as shown in the graph of FIG. 1 representing an in vitro model.

The effects of this can help to decrease, for example, inflammatory response, vasoconstriction, cell migration, cholesterol efflux, foam cell formation, cell recruitment and activation, thrombosis, plaque stability, and/or regulation of lipid and glucose metabolism in adipocytes. Positive control used in above study is Rosiglitazone (see FIG. 1).

2. In-Vivo Evaluation of Curcumin Compositions

The following reported data illustrate results of the above in-vivo testing and the resulting effects.

a. Effect of Curcumin Compositions on Cholesterol Levels in Rat Model

Study was conducted in 12-week-old male Wistar Rats N=8-10 per group.

Four groups were defined as: (1) control without exercise; (2) control with exercise; (3) curcumin composition without exercise; and (4) curcumin composition with exercise Dose: 100 mg/kg, containing about 20 mg of curcuminoids.

The curcumin composition, when administered to the subjects along with exercise shows reduced cholesterol levels compared with subjects not undergoing exercise.

TABLE 4

Effect of curcumin compositions on cholesterol levels

| Blood Chemistries | Groups | | | | |
|---|---|---|---|---|---|
| | Control | Curcumin composition (no exercise) | Exercise | Exercise + Curcumin composition | P |
| Glucose, mg/dL | 86.71 | 83.29 | 78.00 | 79.14 | >0.05 |
| Cholesterol, mg/dL | $62.00^a$ | $54.86^{ab}$ | $61.43^a$ | $42.29^b$ | 0.001 |
| HDL-C, mg/dL | $46.71^a$ | $37.29^{ab}$ | $37.00^b$ | $38.14^b$ | 0.002 |
| LDL, mg/dL | $11.43^a$ | $9.29^{ab}$ | $11.29^a$ | $7.00^b$ | 0.0001 |
| Triglycerides, mg/dL | $84.14^a$ | $71.57^{ab}$ | $63.00^b$ | $54.57^b$ | 0.001 |

Superscripts $a, b, c$, and $d$ indicate that means in the same line without a common superscript differ significantly (P < 0.05).

b. Effect of Curcumin Compositions on Exercise Time and Performance

When curcumin composition is administered to rats along with ongoing exercise activities, the curcumin composition shows improved exercise time and performance.

TABLE 5

Effect of curcumin compositions on exercise time and performance

| Details | Groups | | | |
|---|---|---|---|---|
| | Control | Curcumin composition | Exercise | Exercise + curcumin composition |
| Final weight (grams) | 257.21 ± 6.3 | 261.62 ± 7.6 | 253.62 ± 8.4 | 259.38 ± 5.2 |
| Distance run average per day (meters) | — | — | 1032 ± 54 | 1068 ± 72 |
| Run to exhaustion (minutes) | 70.2 ± 12.4 | 74.7 ± 13.8 | 173.4 ± 17.9 | 185.1 ± 22.0 |

Curcumin compositions can reduce inflammation and exercise produces the muscle fiber damage, inflammation, delayed-onset muscle soreness (DOMS), and various functional deficits. It is now thought that many of these responses to muscle-damaging exercise may be triggered by a large increase in inflammatory cytokines in the working muscle, plasma, and also in the brain to deal with performance deficits associated with exercise-induced muscle damage. The molecular basis of the anti-inflammatory properties of curcumin is linked to its effects on several targets, including transcription factors, growth regulators, and cellular signaling molecules. Curcumin is reported to directly influence the activity of various inflammatory regulators. This study shows different regulatory pathways to reduce muscle damage and to protect from soreness and inflammation.

c. Effect of Curcumin Compositions on Inflammatory Markers

Administration of curcumin composition to exercising rats shows decreased inflammatory response markers.

TABLE 6

Effect of curcumin composition on inflammatory markers

| Blood Chemistries | Groups | | | | |
|---|---|---|---|---|---|
| | Control (no exercise) | Curcumin composition (no exercise) | Exercise | Exercise + Curcumin composition | P |
| LDH, IU/L | 7,535.14 | 7,497.14 | 7,210.14 | 6,908.14 | >0.05 |
| CK, U/L | 15,843.43 | 16,277.86 | 17,198.00 | 16,549.57 | >0.05 |
| Lactate, mg/dL | $8.60^a$ | $7.59^a$ | $5.97^b$ | $4.59^c$ | 0.0001 |

Superscripts $a, b, c$, and $d$ indicate that means in the same line without a common superscript differ significantly (P < 0.05).
IU/L is international units per liter, and U/L is units per liter.

Exercise raises serum enzyme activities which can reveal the state of the muscle and its biochemical adaptation to physical load. Lactate levels right after exercise found little correlation with the level of muscle soreness felt a few days later. These responses to extreme exercise result in an inflammatory-repair response, leading to swelling and soreness that peaks a day or two after the event and resolves a few days later, depending on the severity of the damage. Serum creatine kinase (CK) and lactate dehydrogenase (LDH) give an indication of the degree of metabolic adaptation to physical training of skeletal muscles. Both serum enzymes are involved in muscle metabolism, and their serum concentration is normally very low as a result of physiological wear and tear of the cell. They increase considerably after intensive exercise and in muscle pathology. Monitoring of CK and characterisation of its isoenzymes is widely used in the diagnosis of cardiomyopathies, encephalopathies, and muscle disease. High serum CK activity is a consequence of damage to sarcolemmal membrane. The damage is probably proportional to the duration and intensity of the contraction, and is related to the severity of muscle soreness.

d. Effect of Curcumin Composition on Oxidative Stress and Antioxidant Enzymes

When curcumin composition was administered to rats undergoing exercise, it was seen that such treatment of curcumin to exercising rats decreases the oxidative stress metabolites and improved antioxidant enzymes.

TABLE 7

Effect of curcumin compositions on oxidative stress

| Blood Chemistries | Groups | | | | P |
|---|---|---|---|---|---|
| | Control (no exercise) | Curcumin composition (no exercise) | Exercise | Exercise + Curcumin composition | |
| Muscle MDA, nmol/mg protein | 74.29$^a$ | 56.43$^b$ | 62.71$^b$ | 42.00$^c$ | 0.0001 |
| Muscle SOD, U/mg protein | 0.26$^c$ | 0.36$^b$ | 0.35$^b$ | 0.45$^a$ | 0.0001 |
| Muscle GPx, U/mg protein | 148.00$^b$ | 163.71$^{ab}$ | 161.57$^b$ | 192.43$^a$ | 0.003 |
| Muscle GSH, µg/mg protein | 8.80$^c$ | 12.40$^b$ | 11.89$^b$ | 15.47$^a$ | 0.0001 |

The curcumin composition+exercise exhibited improved antioxidant enzymes and decreased oxidative stress markers, malondialdehyde (MDA) and antioxidant defense systems [e.g. superoxide dismutase (SOD), glutathione peroxidase (GPX) and glutathione (GSH)].

e. Safety Profiles of Curcumin Compositions

TABLE 8

Safety of Curcumin compositions

| Item | Groups | | | | P |
|---|---|---|---|---|---|
| | Control (no exercise) | Curcumin composition (no exercise) | Exercise | Exercise + curcumin composition | |
| AST, U/L | 429.96 | 427.31 | 425.69 | 422.41 | >0.05 |
| ALT, U/L | 74.99 | 75.7 | 79.64 | 75.86 | >0.05 |
| Urea, mg/dl | 48.43 | 48.14 | 49.86 | 46.71 | >0.05 |
| Creatinin, mg/dl | 0.43 | 0.44 | 0.42 | 0.40 | >0.05 |
| ALP, U/L | 477.86 | 479.86 | 482.29 | 460.00 | >0.05 |

(AST being aspartate aminotransferase, ALT being alanine transaminase, and ALP being alkaline phosphatase)

f. Effect of Curcumin Composition on NFκB and IkB

It was seen that curcumin compositions administered to the experimental rats, who are undergoing exercise decreased NFκB and increased IkB (nuclear factor of kappa light polypeptide gene enhancer in B-cells inhibitor). See FIGS. 2 and 3.

FIG. 2 shows that exercise activated NF-kB; while water soluble curcumin composition inhibited exercise-activated NF-κB.

FIG. 3 indicates that exercise increased IkB; while the curcumin composition with exercise significantly increased muscle IkB NFkB is a transcription factor that controls the gene expression of numerous inflammatory proteins. Increased NFkB signaling is thought to decrease insulin action and promote muscle wasting. The data suggest that the NF-kappa B signaling pathway can be activated in a redox-sensitive manner during muscular contraction, presumably due to increased oxidant production.

g. Effect of Curcumin Compositions on Muscle Contraction

When the curcumin compositions are administered to exercise induced rats, it was seen that there were potential benefits of the compositions on muscle contraction. See FIGS. 4 and 5.

FIG. 4 shows that HSP70 expression (70 kilodalton heat shock proteins) is decreased during muscle inactivity, while administration of curcumin compositions without and with exercise increased HSP70.

During evaluation it was seen in FIG. 5 that exercise increased mitochondrial gene expression; while water soluble curcumin compositions with exercise, enhanced muscle mitochondrial gene expression.

Upregulation of HSP70 contributes to the maintenance of muscle fiber integrity and facilitates muscle regeneration and recovery. Evidence supports the loss of HSP70 as a key mechanism which may drive muscle atrophy, contractile dysfunction and reduced regenerative capacity.

Hsp70 serves as an indicator for cellular stress as a molecular chaperone, plays a pivotal role in maintaining cellular homeostasis by preventing apoptosis, influences energy metabolism, facilitates cellular processes in terms of muscular adaptation, and interacts with other signalling pathways.

Exercise activates key stress signals that positively impact major transcriptional pathways that transcribe genes involved in skeletal muscle mitochondrial biogenesis, fusion, and metabolism. Exercise stimulates important key stress signals that control skeletal mitochondrial biogenesis and function.

h. Effect of Curcumin Compositions on Antioxidant Status

The curcumin composition as described herein, when administered to experimental rats along with exercise shows improved antioxidant status. See FIGS. 6 and 7

FIG. 6 indicates that administration of curcumin composition alone or in combination with exercise significantly increased TRX-1, as compared to control rats or only exercising rats. Thioredoxin levels were highest when curcumin compositions were administered to exercising rats.

The curcumin composition as well as curcumin composition with exercise significantly increased SIRT-1 in experimental rats. See FIG. 7.

Thiol antioxidants including thioredoxin (TRX) have a crucial role in controlling cellular redox status. TRX 1 is a defensive protein induced by various stresses and has anti-oxidative, anti-apoptotic effect.

Deacetylases such as sirtuins (SIRTs) convert NAD to nicotinamide (NAM). Nicotinamide phosphoribosyl transferase (Nampt) is the rate-limiting enzyme in the NAD salvage pathway responsible for converting NAM to NAD to maintain cellular redox state and anti-inflammatory effects. SIRT1 is a regulator of mitochondrial biogenesis.

i. Effect of Curcumin Compositions on Inflammation and Oxidative Stress

Effect of curcumin composition was evaluated in rats which were not exercising and it was compared with the effect of curcumin compositions in rats undergoing rigorous exercise to check on inflammation and oxidative stress. See FIGS. 8 and 9.

In FIG. 8, increased Nrf2 shows the curcumin composition to have anti-inflammatory effects. See also FIG. 9 where increased HO-1 also shows curcumin composition to have anti-inflammatory effects.

Exercise increased expression and activity of the nuclear factor erythroid 2-related factor (Nrf2), a transcriptional regulator of the cellular anti-oxidant system, and decreased expression and activity of nuclear factor kappa beta (NF-κB), a mediator of inflammatory molecules, in the nucleus of testicular cells.

Nuclear factor erythroid 2-related factor 2 (Nrf2) activates expression of cytoprotective genes to enable cell adaptation to protect against oxidative stress.

Heme-oxygenase-1 (HO-1) attenuates immobilization-induced skeletal muscle atrophy through the suppression of protein degradation via its anti-oxidant and anti-inflammatory properties. HO-1 is an antioxidant stress protein that is mainly induced by reactive oxygen species, inflammatory cytokines and hyperthermia.

j. Effect of Curcumin Composition on Glucose Transporter Type 4

Effect of Curcumin composition on mitochondrial biogenesis was evaluated in rat model, who were maintained sedentary as well as in those who were exercising animals, to evaluate effect of curcumin to enhance exercise performance. See FIGS. 10 and 11.

FIG. 10 shows that Glut4 (glucose transporter type 4) increased in rats administered with the curcumin composition and also in models administered with curcumin composition and undergoing simultaneous exercise.

Exercise induces an increase in the GLUT4 isoform of the glucose transporter. This increase in GLUT4 occurs in parallel with, and is mediated by, the same signals and some of the same transcription factors as the increase in mitochondrial biogenesis.

cumin and at least one pharmaceutically or nutraceutically acceptable excipient selected from a group, but not limited to hydrophilic carrier, fat, antioxidant, diluents, surfactant, solubilizer and so on or the combination thereof. The compositions can be further formulated as granules, beadlets, tablets, capsules, oil suspensions, soft gel capsules, and so on and exhibit enhanced solubility.

The study design chosen was a balanced, open label, two-treatment, two-period, single dose, bioavailability study. Twelve healthy (12) subjects were recruited for the study and were asked to avoid consumption of food containing rich turmeric powder or extract for 24 hours preceding each period. A single dose of the curcumin composition (i.e. capsule form) was administered, equivalent to 1 gm of curcuminoids, during the study. The following supplements were used for the purpose of the study:

Supplement 1—comprising curcumin composition (500 mg Capsule equivalent to 1 gm of curcuminoids) was administered as a single dose of two capsules of curcumin composition 500 mg.

Supplement 2—comprising curcumin Ultrasol Dry Nutrient System (curcumin compositions formulated using at least one excipient such as hydrophilic carrier) (250 mg Capsule equivalent to 1 gm of curcuminoids) was administered as a single dose of four capsules of Curcumin Ultrasol Dry Nutrient System 250 mg.

Blood was drawn from each subject just prior to dosing and at 1, 2, 4, 6, 8, and 24 hours post-dose. The blood samples drawn at different time intervals were centrifuged and the curcumin in plasma was measured through HPLC technique. $C_{max}$, AUC, $T_{max}$, $T_{1/2}$, Kel and Geometric mean were calculated.

Results: Mean pk values and Geometric mean for Curcumin compositions (supplement 1 and 2)

| Product | | $C_{max}$ ng/ml | $T_{max}$ | $AUC_{0-T}$ ng/ml * h | $AUC_{INF}$ ng/ml * h | Kel (hr) | $T_{1/2}$ (hr) |
|---|---|---|---|---|---|---|---|
| Curcumin water soluble composition: supplement 1 | Geometric mean | 13.263 ± 10.13 10.486 | 8.250 ± 9.98 4.059 | 98.774 ± 63.9 80.968 | 80.433 ± 6.38 80.269 | 0.104 ± 0.04 0.098 | 7.516 ± 3.38 7.066 |
| Curcumin UltraSol Nutrient System: Supplement 2 | Geometric mean | 31.347 ± 10.13 29.502 | 2.333 ± 9.98 2.000 | 217.467 ± 63.9 174.09 | 541.929 ± 6.37 279.46 | 0.067 ± 0.04 0.052 | 20.671 ± 3.38 13.42 |

GLUT4 is the insulin-regulated glucose transporter found in heart tissue, skeletal muscle, and adipose tissues. It is responsible for insulin-regulated glucose disposal. GLUT4 is regulated by insulin; therefore, its role is defected when insulin is not functioning in the right way. The major physiological action of insulin is to increase glucose uptake and storage in adipose tissue, skeletal muscle, and heart.

FIG. 11 shows the effect of curcumin compositions herein on various body markers.

Example 7

Bioavailability Study of Water Soluble Curcumin Compositions

The following reported data provides a comparative bioavailability study carried out on curcumin compositions, as described herein. The compositions are prepared using cur- Both curcumin compositions and the doses were well tolerated and there were no adverse events reported during the study period.

The invention claimed is:

1. A method of improving muscle performance, endurance capacity and resistance to fatigue, comprising administering to a subject undergoing exercise a composition comprising an active ingredient containing curcuminoids and one or more hydrophilic carriers, which are formulated into a water soluble solid dispersion, the administering being about 20 mg/kg body weight of the curcuminoids daily for a period of weeks, wherein the administering of said composition increases mitochondrial biogenesis and reduces oxidative muscle stress as compared to one who is sedentary without being administered the composition, undergoing exercise without being administered the composition, or sedentary while being administered the composition.

2. The method as claimed in claim 1, wherein the subject is a mammal.

3. The method as claimed in claim 1, wherein the administering increases mitochondrial biogenesis by increasing mitochondrial biomass, oxygen consumption, and mitochondrial aerobic capacity.

4. The method as claimed in claim 1, wherein the administering reduces oxidative muscle stress by decreasing release of inflammatory markers, inflammatory cytokines, and oxidative stress metabolites.

5. The method as claimed in claim 1, wherein the administering reduces oxidative muscle stress by improving a level of an antioxidant enzyme.

6. The method as claimed in claim 4, wherein the administering reduces oxidative muscle stress by decreasing at least one of the inflammatory markers selected from the group consisting of lactate dehydrogenase (LDH), serum creatine kinase (CR), and lactate.

7. The method as claimed in claim 5, wherein the administering reduces oxidative muscle stress by improving a level of at least one of the antioxidant enzymes selected from the group consisting of muscle malondialdehyde (MDA), superoxide dismutase (SOD), glutathione peroxidase (GPx), and glutathione.

8. The method as claimed in claim 4, wherein the administering enhances exercise performance by activating PPAR gamma receptors, thus regulating fatty acid and cholesterol blood levels.

9. The method as claimed in claim 1, wherein the administering improves exercise time and performance by reducing muscle fiber damage, delaying onset muscle soreness, and reducing muscle inflammation.

10. The method as claimed in claim 1, wherein the composition further comprises by weight percentage of the composition 1 to 25 wt % of one or more fats and 1 to 10 wt % of one or more antioxidants, and the one or more hydrophilic carriers is 10-90 wt %.

11. The method as claimed in claim 1, wherein the active ingredient of the composition is curcumin.

12. The method as claimed in claim 1, wherein the about 20 mg/kg body weight of the curcuminoids is included within a 100 mg/kg body weight dose, the 100 mg/kg body weight dose including about 65-70 mg/kg body weight of the one or more hydrophilic carriers, about 4-8 mg/kg body weight of one or more antioxidants, and about 4-8 mg/kg body weight of one or more fats.

13. The method as claimed in claim 1, wherein the period of weeks is six weeks.

14. The method as claimed in claim 2, wherein the mammal is a human.

* * * * *